United States Patent [19]
Huttenhoff et al.

[11] Patent Number: 5,920,263
[45] Date of Patent: Jul. 6, 1999

[54] DE-ESCALATION OF ALARM PRIORITIES IN MEDICAL DEVICES

[75] Inventors: John P. Huttenhoff, Madison; Trent L. Williams, Sun Prairie; Christopher R. Goodrich, McFarland; Graham B. Lukey, Madison, all of Wis.

[73] Assignee: Ohmeda, Inc., Liberty Corner, N.J.

[21] Appl. No.: 09/096,238

[22] Filed: Jun. 11, 1998

[51] Int. Cl.⁶ .............................. G08B 7/06; G08B 25/14
[52] U.S. Cl. ........................... 340/573; 340/679; 340/691
[58] Field of Search ...................................... 340/679, 691, 340/573

[56] References Cited

U.S. PATENT DOCUMENTS

| | | |
|---|---|---|
| 4,501,531 | 2/1985 | Bilstad et al. ........................ 340/691 |
| 5,262,944 | 11/1993 | Weisner et al. ........................ 340/573 |

*Primary Examiner*—Glen Swann
*Attorney, Agent, or Firm*—Andrus, Sceales, Starke & Sawall

[57] ABSTRACT

An alarm prioritizing system for use with a medical device categorizes the alarms into high, medium and low priority alarms. With the medium and high priority alarms, there is a visual indication and a audible sound that cannot be fully muted. With certain alarms, however, the operator can, by a positive and deliberate input, de-escalate the alarm priority from a medium priority alarm to a low priority alarm where the audible sound is muted and only a visual indication is thereafter provided. There is a time delay between the time the user actually starts the de-escalation process before it is effected to enable the user to properly identify the alarm and its location on a visual display panel. As a further feature, the same visual indication shifts from a medium priority alarm location to a low priority alarm location.

10 Claims, 3 Drawing Sheets

DE-ESCALATION OF ALARM PRIORITIES IN MEDICAL DEVICES

BACKGROUND

This invention relates to medical devices and, more particularly, to a system that changes the priority of alarms on medical devices.

In present medical devices, there are numerous alarm systems that are activated under fault conditions to alert the user to the existence of those fault conditions. In such devices, there are a wide variety of alarms and many conditions that are continuously monitored. Many fault conditions can occur with respect to the patient or with respect to certain conditions of the medical device itself.

In general, the types of alarms are classified into certain categories according to the severity of the consequences of the alarm condition, that is, the alarm may be classified as a high, medium or low priority. The annunciation of the particular alarm in any one of those categories is generally prescribed by various standards, that is, if the alarm is a high or medium priority alarm, there generally must be a repetitive, audible alarm and the user has a limited ability to silence such alarm.

On the other hand, the alarms that are classified into the low priority are of lesser severity. A repeated audio component or annunciation is not a requirement, and only a visual display alerts the user to the continued existence of an alarm condition.

Once classified into one of the foregoing categories, the manner of annunciation of the alarm is mandated, as described, by various standards. However, it is generally within the judgment of the manufacturer of the medical device as to what particular alarm will be placed into any of the categories.

One of the difficulties with any audio alarm is that they can become distracting in the clinical environment, particularly the hospital operating room, where there are already many other distractions. The continual sounding of an audible alarm can be further distracting and bothersome to the clinician. As a result, there is a tendency to classify many alarms as low priority and to provide only a visual alarm indication to avoid the multitude of sounds of alarms in the hospital environment. The difficulty with such approach, however, is that the clinician may miss the non-repeating low priority audio, if provided, and therefore miss the fact that an alarm condition exists that should be at least brought to the attention of the operating personnel.

The dilemma in today's medical devices is that classification of the alarms as high or medium priority creates the possibility of numerous audio alarms that are bothersome and are distracting to the clinician potentially inhibiting the clinicians complete attention to the particular operation. Alternatively, the alarm condition can be classified as a low priority with the inherent risk that an alarm condition may not sufficiently gain the clinician's attention.

Accordingly, it would be advantageous for certain medium priority alarms to be able to be downgraded or de-escalated into the low priority category once the user has been made aware of a given condition, so that the potentially distracting audible sound is removed from the already busy and sometimes noisy surroundings in the clinical environment and is not a further distraction to the clinician. It is not desirable that the alarm completely go away since its presence is needed as a reminder of the fault condition. It would also be advantageous if the de-escalation of the alarm category is only allowed through some positive, deliberate act by the clinician.

SUMMARY OF THE INVENTION

In accordance with the present invention, there is provided an alarm system that can reduce the potentially distracting audible alarms in the medical environment and yet maintain the alarm condition in a form that provides an initial alarm at an appropriate level of concern for the condition, and then is continually available to the attending clinician, to maintain continued awareness of the alarm condition.

Accordingly, in carrying out the present invention, certain alarms that are normally classified as medium priority alarms are allowed to be reclassified or de-escalated to the low priority category upon recognition of the alarm and upon deliberate action on the part of the clinician. The deliberate action by the clinician ensures that the alarm has been noticed by the clinician and a positive act by the clinician is necessary to de-escalate the alarm to a low category. In the preferred embodiment, the alarm is held for a predetermined period of time as a medium priority alarm, even after a deliberate acknowledgment, prior to de-escalation, so that the clinician can locate and identify the alarm.

Thereafter the category of the alarm is downgraded and its location on the visual alarm panel moved to a lesser position of seriousness, that is, the visual indication of the alarm condition is moved from an area where the medium priority alarms are located to the area of the visual display panel where the low priority alarms are located. Thus, the audible alarm is silenced by some deliberate action on the part of the clinician and the visual indication is also de-escalated to a different location on the visual display panel, so as to remain as an active alarm visually but not cause a further audible distraction to the clinician. The clinician can thus concentrate on the patient and not be potentially distracted by a continual audio alarm that the clinician has chosen to de-escalate to a lower priority. Such de-escalation is particularly useful for alarms for equipment or monitoring failures, or for a change in the machine operational state where it is important that the user be made aware that some piece of functionality or monitoring has been lost, but once the user understands the alarm, acknowledges it, and decides to continue to use the equipment to complete the case, a constant audio reminder would be a nuisance.

DETAILED DESCRIPTION OF THE INVENTION

Figure 1:
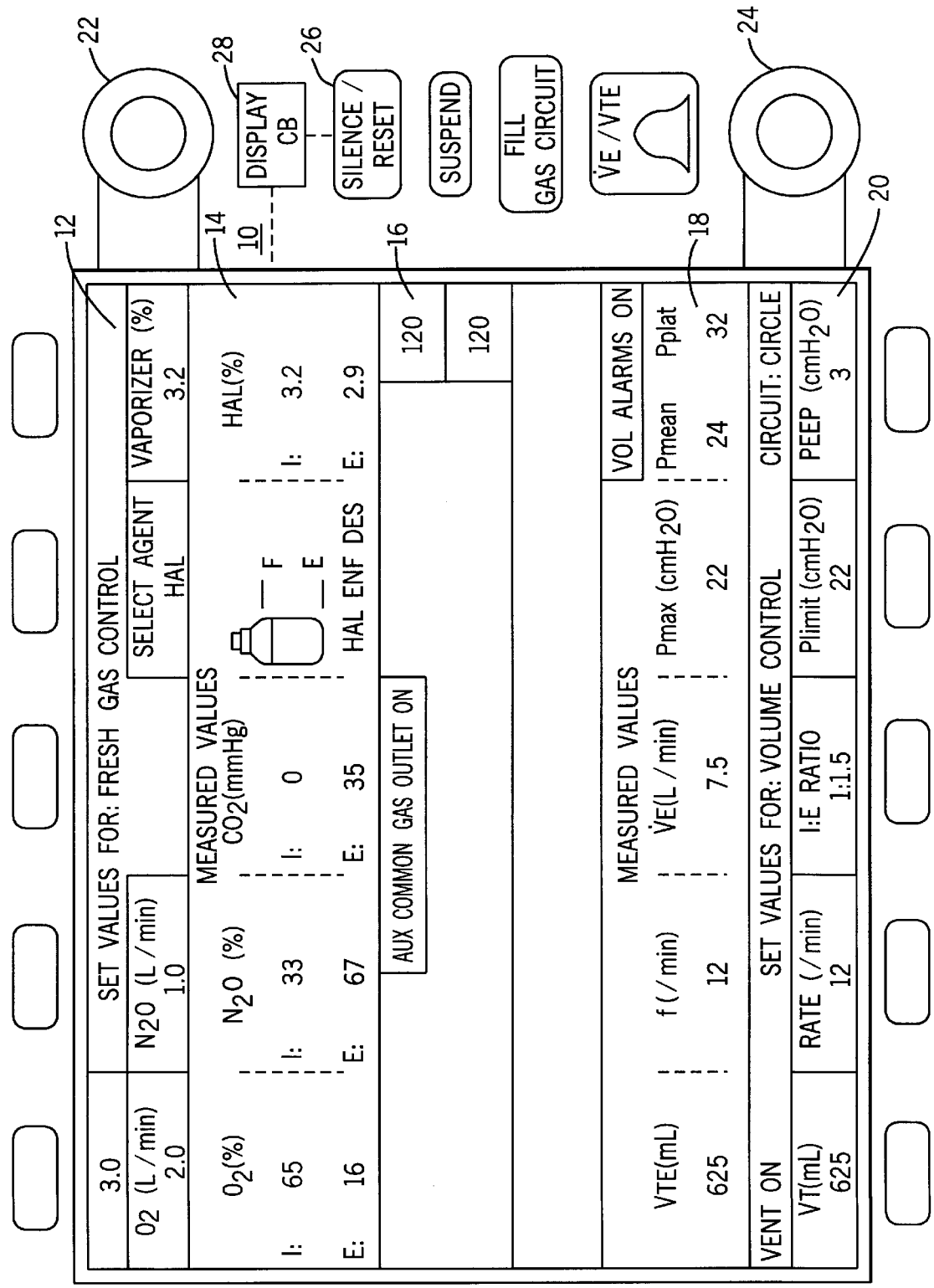
FIG. 1 is a schematic view of a visual display panel that is used with the present invention showing an alarm condition.

Referring now to FIG. 1, there is shown a schematic view of a visual display panel 10 that is used with the present invention. Basically, the display panel 10 is typical of a CRT or flat panel display used with medical devices and which provides a display to the user of various operating conditions of that medical device as well as to provide an indication of any alarm conditions that may be in effect at the time.

As shown, the typical display panel 10 is divided into a plurality of horizontally disposed sections, and may include a section 12 that comprises controls and settings relating to the gas delivery control, a section 14 setting forth the measured values including oxygen concentration, nitrous oxide concentration and the selection and concentration of the anesthetic agent. A further section is an alarm panel section 16 that can be used to display a visual indication of any alarm conditions that may be in effect at the time. Further horizontally oriented sections may display the measured values at section 18, setting forth ventilator parameters and a section 20 that displays set values for the medical ventilator. All of the above are fairly standard displays for medical devices, such as an anesthesia machine, and the specific orientation of any of the various displays and selection parameters can, of course, vary with the particular placement by the manufacturer of the medical device. The display panel 10 generally will also include various knobs 22 and 24 for selecting and changing the values of the various parameters of supplying a respirable gas to a patient during an operation.

In addition, a user input, in this example in the form of an alarm silence button 26 is shown and which may interconnect with. a display circuit board including a central processing unit (CPU), as depicted by the box 28.

As can be seen in the FIG. 1, there is an example alarm indication as "Aux. Common gas outlet On" that is being displayed and that display may be in a area of the display panel 10 that is reserved for alarms of a medium priority and therefore is an alarm that will be readily noticed by the clinician. The area that provides a visual display of medium priority alarm may be at various locations on the display panel 10 and that area will become recognized by the clinician and continuously reviewed to determine what alarms are active.

Figure 2:
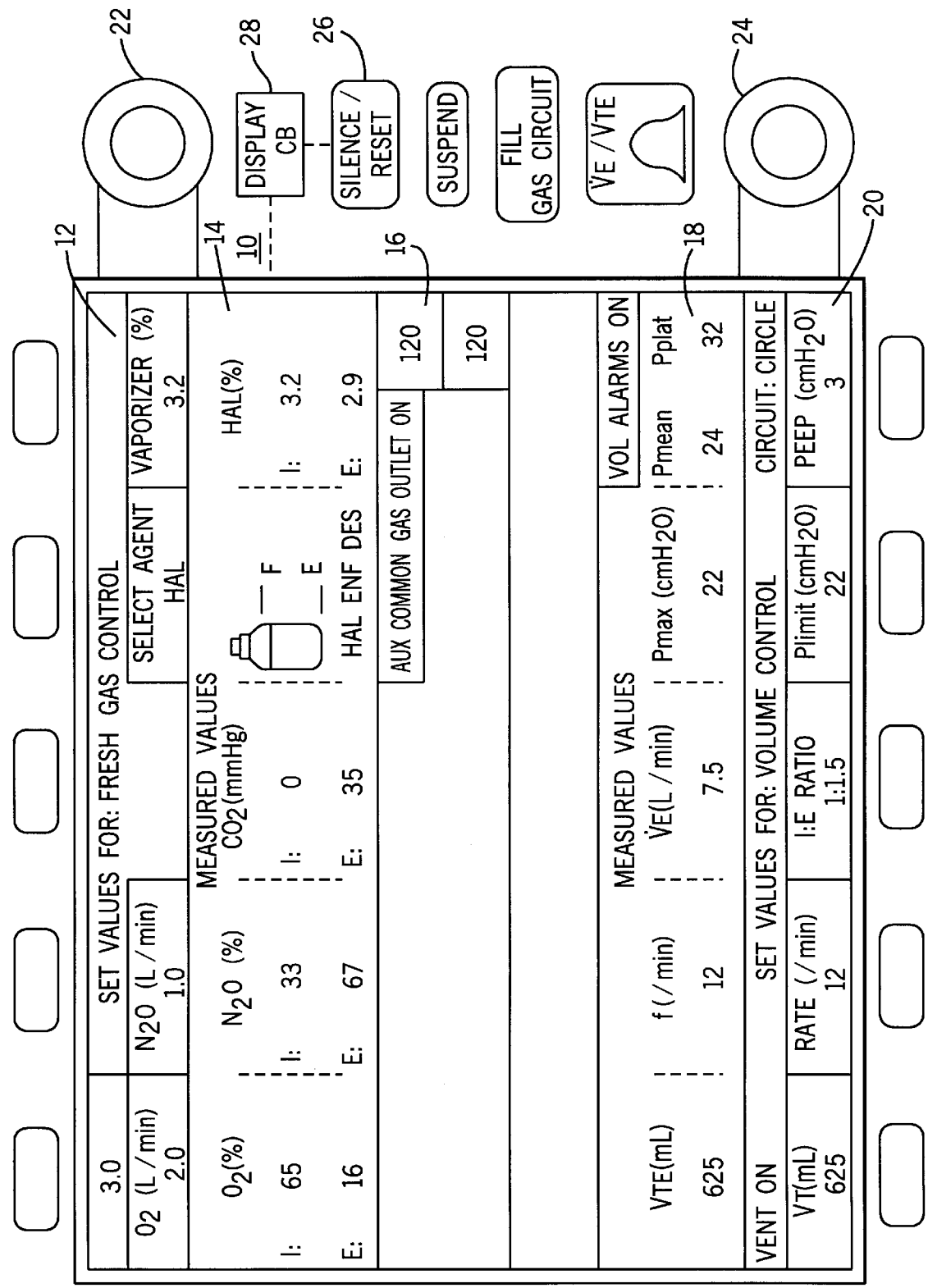
FIG. 2 is a schematic view of the visual display panel of FIG. 1 showing alarm condition in a different position.

In FIG. 2, it can be seen that the same display panel 10 is shown but the particular alarm display of "Aux common gas outlet ON" has been moved to a different location than in FIG. 1 and, as will be explained, that new location may be in the area where low priority alarm are normally displayed and which is recognized by the clinician to be of lesser priority alarm conditions. Again, that location is shown in FIG. 2 for illustrative purposes and could be an any number of locations on the display panel 10 as long as the clinician recognizes and understands the priority of the alarms at that particular location.

Figure 3:
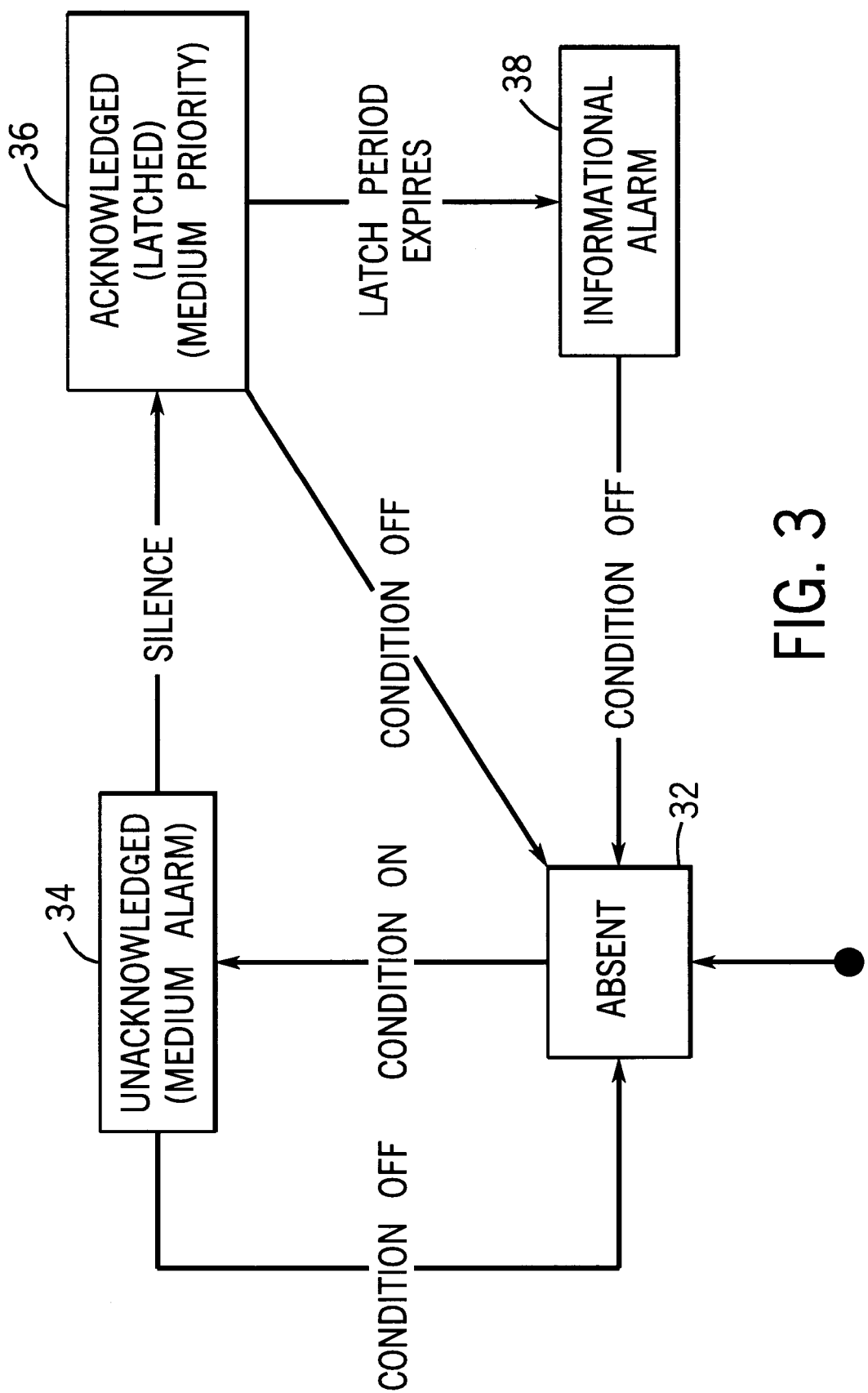
FIG. 3 is a flow chart of the various steps taken in carrying out the present invention.

In FIG. 3, there is shown a state diagram of the various steps that are undertaken in carrying out the present invention. In an initial state, when the alarm condition is inactive, the system is in the Absent state depicted by the Box 32. When the alarm condition becomes active, the system transitions to the Unacknowledged Medium Priority alarm state depicted by Box 34. At this point, the alarm is of the medium priority category and an audible signal is transmitted to alert the user of the alarm condition. In addition, since the alarm is of the medium priority category, in conventional medical devices an audible signal is sounded which can only be silenced for a limited period of time. Thus, the audio sound becomes a persistent noise that is a potential distraction to the clinician. Some alarms, however, which are of the medium priority category and which have an audible signal, are predetermined in accordance with the present invention by the medical device to able to be de-escalated, because of their nature, to a low priority category and thus eliminating the potentially distracting audible sound.

That de-escalation requires some positive, deliberate act by the clinician and one such act, in the embodiment shown, is by the clinician pushing the alarm silence button 26. Other inputs may be employed, depending on the nature of the alarm, to facilitate the deliberate act by the clinician to allow de-escalation of the alarm. Again, in the embodiment shown, the activation of the user input by means of the silence button 26 activates a predetermined latching time period, depicted by the box 36 and a period of time passes to enable the clinician to have time to look at the display panel 10 to see what the particular alarm condition is and to note its position on the display panel 10. The time delay is preferably from between about 5 and 30 seconds. Accordingly, after that predetermined latched period of time has elapsed, the system automatically de-escalates the alarm category to the low priority category alarm, shown by box 38 and thereafter there is no audible sound, but only a visual notice to the clinician as a continual reminder that the alarm condition still exists. As shown in FIGS. 1 and 2, that alarm visual indication may move from one position on the display panel 10 where the medium priority alarms are normally displayed to another position where the low priority alarms are generally located so that the alarm itself is de-escalated to a differing position on the display panel 10 and remains as a lesser, but still a visual alarm, to the clinician.

We claim:

1. An alarm system for recognizing and alerting a user to a fault condition in a medical device, said alarm system comprising a means to activate an alarm responsive to detection of the fault condition, said alarm system having an audible annunciation and a display panel for displaying a visual indication of said alarm, said alarm having a first state wherein said audible annunciation is activated and said visual indication is activated to display said alarm at a first location on said display panel, said alarm further having a second state wherein said visual alarm is activated to display said alarm at a second location on said display panel and said audible alarm is silenced and means operable by user action to de-escalate said alarm from said first state to said second state, whereby said visual alarm indication is displayed on said display panel at said second location and said audible annunication is muted.

2. An alarm system for a medical device as defined in claim 1 wherein said alarm system includes an input device operable by the user action and a timer to provide a predetermined time delay between the operation of said input device and the de-escalation of said alarm from said first state to said second state.

3. An alarm system for a medical device as defined in claim 2 wherein said time delay is between 5 seconds and 30 seconds.

4. An alarm system for a medical device as defined in claim 2 wherein said medical device is from the group comprising anesthesia delivery devices, breathing gas delivery devices, and patient monitors.

5. A system for the de-escalating of an alarm priority in a medical device, said system comprising:

sensing means to monitor the operation of said medical device and to determine the existence of a predetermined fault condition and to produce a signal when said fault condition occurs, a display panel for receiving said signal from said sensing means to indicate a visual notice of the fault condition, an audible device receiving the signal from said sensing means to provide an audible annunciation when said fault condition is determined, means to categorize a plurality of said fault conditions as a first category based upon the consequences of said fault condition wherein said visual indication is provided on said display panel and said audible annunciation is provided, wherein at least one of said first category fault conditions is a predetermined fault condition representative of a lesser consequence fault condition, input means operable by a user to de-escalate only said at least one predetermined fault condition of said plurality of fault conditions from said first category to a second, lower fault category of lesser consequences wherein said visual indication is provided on said display panel and said audible annunciation is muted.

6. A system for the de-escalating of an alarm priority in a medical device as defined in claim 5 wherein said input means further includes a timer that provides a predetermined time period interposed between the operation of the input means by the user and the de-escalating of said category.

7. A system for the de-escalating of an alarm priority in a medical device as defined in claim 5 wherein said medical device is from the group comprising of anesthesia delivery devices, breathing gas delivery devices and patient monitors.

8. In an alarm system for a medical device with prioritized alarms, a method of controlling the priority of alarms activated upon various fault conditions, said method comprising:

categorizing alarms of the medical device into at least two categories of fault conditions depending upon the higher or lower consequences of the fault condition, providing an audible alarm and a visual alarm upon the detection of a fault condition of the higher consequences, providing a visual alarm with non-repeating or no audio component upon the detection of a fault condition of the lower consequences, and providing an input means to enable the user to deliberately de-escalate the fault category from the higher category to the lower category.

9. A method for the de-escalating of an alarm priority in a medical device as defined in claim 8 wherein said medical device is from the group comprising of anesthesia delivery devices, breathing gas delivery devices and patient monitors.

10. An alarm system for recognizing and alerting a user to a fault condition in a medical device, said alarm system having alarms activated by fault conditions, said alarms being prioritized into higher and lower priorities depending upon the severity of the consequences of the particular alarm condition activating the alarm, said alarms having different means for communicating the alarm to a user depending on the higher or lower priority, and an input means to enable a user to de-escalate at least one but not all of said alarms to reduce said priority from the higher priority alarm to the lower priority alarm.

* * * * *